(12) United States Patent
McSheffrey, Sr. et al.

(10) Patent No.: US 8,350,693 B2
(45) Date of Patent: Jan. 8, 2013

(54) TRANSMISSION OF DATA TO EMERGENCY RESPONSE PERSONNEL

(75) Inventors: John J. McSheffrey, Sr., Hingham, MA (US); John J. McSheffrey, Jr., Needham, MA (US); Brendan T. McSheffrey, Newton, MA (US)

(73) Assignee: en-Gauge, Inc., Rockland, MA (US)

( * ) Notice: Subject to any disclaimer, the term of this patent is extended or adjusted under 35 U.S.C. 154(b) by 0 days.

(21) Appl. No.: 13/356,307

(22) Filed: Jan. 23, 2012

(65) Prior Publication Data

US 2012/0119917 A1    May 17, 2012

Related U.S. Application Data

(63) Continuation of application No. 13/079,440, filed on Apr. 4, 2011, now abandoned, which is a continuation of application No. 11/856,618, filed on Sep. 17, 2007, now Pat. No. 7,961,089, which is a continuation of application No. 10/863,668, filed on Jun. 8, 2004, now Pat. No. 7,271,704.

(51) Int. Cl.
*G08B 1/00* (2006.01)

(52) U.S. Cl. .......... 340/531; 340/286.05; 340/606; 340/517; 340/521; 340/539.16; 340/539.17; 340/539.22; 340/539.26

(58) Field of Classification Search ........... 340/286.05, 340/606, 517, 521, 539.16, 539.17, 539.22, 340/539.26
See application file for complete search history.

(56) References Cited

U.S. PATENT DOCUMENTS

| | | |
|---|---|---|
| 992,456 A | 5/1909 | Casey |
| 2,670,194 A | 2/1954 | Hansson |
| 3,145,375 A | 8/1964 | Webb |
| 3,333,641 A | 8/1967 | Hansom |
| 3,664,430 A | 5/1972 | Sitabkhan |
| 3,735,376 A | 5/1973 | Kermer et al. |
| 3,946,175 A | 3/1976 | Sitabkhan |
| 4,003,048 A | 1/1977 | Weise |
| 4,015,250 A | 3/1977 | Fudge |
| 4,034,697 A | 7/1977 | Russell |
| 4,051,467 A | 9/1977 | Galvin |
| 4,100,537 A | 7/1978 | Carlson |
| 4,101,887 A | 7/1978 | Osborne |
| 4,119,153 A | 10/1978 | Avant |

(Continued)

FOREIGN PATENT DOCUMENTS

DE    3731793    3/1989

(Continued)

OTHER PUBLICATIONS

"U.S. Appl. No. 11/856,618, Non-Final Office Action mailed Sep. 28, 2010", 6 pgs.

(Continued)

*Primary Examiner* — Daryl Pope
(74) *Attorney, Agent, or Firm* — Strategic Patents, P.C.

(57) ABSTRACT

A system includes a fire extinguisher station having a number of sensors to detect various predetermined conditions that can be communicated in alarms to a central station. The central station receives alarms from the fire extinguisher and determines whether to contact emergency personnel and/or building maintenance personnel. Other items of emergency equipment can be included in the system for improved detection and response to emergency conditions.

20 Claims, 12 Drawing Sheets

U.S. PATENT DOCUMENTS

| | | | |
|---|---|---|---|
| 4,125,084 A | 11/1978 | Salmonsen et al. | |
| 4,143,545 A | 3/1979 | Sitabkhan | |
| 4,184,377 A | 1/1980 | Hubbard | |
| 4,246,046 A | 1/1981 | Lameyer | |
| 4,279,155 A | 7/1981 | Balkanli | |
| 4,289,207 A | 9/1981 | Wernert | |
| 4,303,395 A | 12/1981 | Bower | |
| 4,342,988 A | 8/1982 | Thompson et al. | |
| 4,360,802 A | 11/1982 | Pinto | |
| 4,418,336 A * | 11/1983 | Taylor | 340/571 |
| 4,419,658 A | 12/1983 | Jarosz et al. | |
| 4,436,414 A | 3/1984 | Kamiyama et al. | |
| 4,531,114 A | 7/1985 | Topol et al. | |
| 4,548,274 A | 10/1985 | Simpson | |
| 4,586,383 A | 5/1986 | Blomquist | |
| 4,592,301 A * | 6/1986 | Monte | 116/67 R |
| 4,599,902 A | 7/1986 | Gray | |
| 4,613,851 A | 9/1986 | Hines | |
| 4,697,643 A | 10/1987 | Sassier | |
| 4,805,448 A | 2/1989 | Armell | |
| 4,823,116 A | 4/1989 | Kitchen, III et al. | |
| 4,823,788 A | 4/1989 | Smith et al. | |
| 4,835,522 A | 5/1989 | Andrejasich et al. | |
| 4,866,423 A | 9/1989 | Anderson et al. | |
| 4,887,291 A | 12/1989 | Stillwell | |
| 4,890,677 A | 1/1990 | Scofield | |
| 4,928,255 A | 5/1990 | Brennecke et al. | |
| 4,979,572 A | 12/1990 | Mikulec | |
| 5,123,409 A | 6/1992 | Sheffield et al. | |
| 5,153,567 A | 10/1992 | Chimento | |
| 5,153,722 A | 10/1992 | Goedeke et al. | |
| 5,224,051 A | 6/1993 | Johnson | |
| 5,357,242 A | 10/1994 | Morgano et al. | |
| 5,388,570 A | 2/1995 | Wassil | |
| 5,400,246 A | 3/1995 | Wilson et al. | |
| 5,460,228 A | 10/1995 | Butler | |
| 5,475,614 A | 12/1995 | Tofte et al. | |
| 5,486,811 A | 1/1996 | Wehrle et al. | |
| 5,534,851 A | 7/1996 | Russek | |
| 5,578,993 A | 11/1996 | Sitabkhan et al. | |
| 5,593,426 A | 1/1997 | Morgan et al. | |
| 5,596,501 A | 1/1997 | Comer et al. | |
| 5,613,778 A | 3/1997 | Lawson | |
| 5,652,393 A | 7/1997 | Lawson | |
| 5,706,273 A | 1/1998 | Guerreri | |
| 5,775,430 A | 7/1998 | McSheffrey | |
| 5,781,108 A | 7/1998 | Jacob et al. | |
| 5,793,280 A | 8/1998 | Hincher | |
| 5,808,541 A | 9/1998 | Golden | |
| 5,848,651 A | 12/1998 | McSheffrey et al. | |
| 5,853,244 A | 12/1998 | Hoff et al. | |
| 5,864,287 A | 1/1999 | Evans, Jr. et al. | |
| 5,877,426 A | 3/1999 | Hay et al. | |
| 5,936,531 A | 8/1999 | Powers | |
| 5,952,919 A | 9/1999 | Merrill | |
| 6,014,307 A | 1/2000 | Crimmins | |
| 6,114,823 A | 9/2000 | Doner et al. | |
| 6,125,940 A | 10/2000 | Oram | |
| 6,128,576 A | 10/2000 | Nishimoto et al. | |
| 6,141,584 A | 10/2000 | Rockwell et al. | |
| 6,155,160 A | 12/2000 | Hochbrueckner | |
| 6,168,563 B1 | 1/2001 | Brown | |
| 6,240,365 B1 | 5/2001 | Bunn | |
| 6,270,455 B1 | 8/2001 | Brown | |
| 6,289,331 B1 | 9/2001 | Pedersen et al. | |
| 6,301,501 B1 | 10/2001 | Cronin et al. | |
| 6,302,218 B1 | 10/2001 | McSheffrey et al. | |
| 6,311,779 B2 | 11/2001 | McSheffrey et al. | |
| 6,317,042 B1 | 11/2001 | Engelhorn et al. | |
| 6,327,497 B1 | 12/2001 | Kirchgeorg et al. | |
| 6,336,362 B1 | 1/2002 | Duenas | |
| 6,351,689 B1 | 2/2002 | Carr et al. | |
| 6,357,292 B1 | 3/2002 | Schultz et al. | |
| 6,401,713 B1 | 6/2002 | Hill et al. | |
| 6,450,254 B1 | 9/2002 | Hoyle et al. | |
| 6,488,099 B2 | 12/2002 | McSheffrey et al. | |
| 6,496,110 B2 | 12/2002 | Peterson et al. | |
| 6,542,076 B1 | 4/2003 | Joao | |
| 6,585,055 B2 | 7/2003 | Mcsheffrey et al. | |
| 6,587,049 B1 | 7/2003 | Thacker | |
| 6,598,454 B2 | 7/2003 | Brazier et al. | |
| 6,646,545 B2 | 11/2003 | Bligh | |
| 6,735,473 B2 | 5/2004 | Kolder et al. | |
| 6,853,309 B1 | 2/2005 | Schröter | |
| 6,856,251 B1 | 2/2005 | Tietsworth et al. | |
| 7,259,656 B1 * | 8/2007 | Wright | 340/286.14 |
| 7,271,704 B2 | 9/2007 | McSheffrey et al. | |
| 7,728,715 B2 | 6/2010 | Riedel et al. | |
| 7,891,435 B2 | 2/2011 | McSheffrey et al. | |
| 7,961,089 B2 | 6/2011 | McSheffrey et al. | |
| 2001/0025713 A1 | 10/2001 | Mcsheffrey et al. | |
| 2001/0052681 A1 | 12/2001 | Deavila | |
| 2003/0071736 A1 | 4/2003 | Brazier et al. | |
| 2003/0116329 A1 | 6/2003 | McSheffrey et al. | |
| 2003/0135324 A1 | 7/2003 | Navab | |
| 2003/0189492 A1 | 10/2003 | Harvie | |
| 2004/0017471 A1 | 1/2004 | Suga et al. | |
| 2010/0171624 A1 | 7/2010 | McSheffrey et al. | |
| 2010/0245570 A1 | 9/2010 | Riedel et al. | |
| 2011/0109454 A1 | 5/2011 | Mcsheffrey, Sr. et al. | |
| 2011/0241873 A1 | 10/2011 | Mcsheffrey et al. | |

FOREIGN PATENT DOCUMENTS

| | | |
|---|---|---|
| FR | 2340109 | 9/1977 |
| FR | 2515845 | 5/1983 |
| FR | 2676931 | 12/1992 |
| WO | WO-81/02484 | 9/1981 |
| WO | WO-94/11853 | 5/1994 |
| WO | WO-01/46780 | 6/2001 |
| WO | WO-01/93220 | 12/2001 |
| WO | WO-03/076765 | 9/2003 |
| WO | WO-03/098908 | 11/2003 |

OTHER PUBLICATIONS

"PCT/US2004/022019 International Search Report", PCT/US2004/022019 Aug. 7, 2004 , all.

"Exciting new Products for Measuring Flow and Pressure", Cole-Parmer Brochure Canada Apr. 23, 1996 , 1 pg.

""Help That Comes Too Late is as Good as No Help at All—The Fire Extinguisher Alarm System Gives Immediate Help"", Invention Technologies, Inc. Press release.

"U.S. Appl. No. 12/684,344, Non-Final Office Action mailed Apr. 27, 2011", , 23.

"U.S. Appl. No. 13/079,440, Non-Final Office Action mailed Jul. 22, 2011", , 11.

"U.S. Appl. No. 13/356,307, Non-Final Office Action mailed Mar. 27, 2012", , 3.

"U.S. Appl. No. 10/614,948, Notice of Allowance mailed Dec. 8, 2010", , 7.

"U.S. Appl. No. 11/856,618, Notice of Allowance mailed Feb. 3, 2011", , 5.

"U.S. Appl. No. 12/716,366, Non-Final Office Action mailed Sep. 15, 2010", , 3 Pgs.

"NFPA 10 Standard for Portable Fire Extinguishers", Nat'l Fire Protection Assoc. 1998 Edition , pp. 10.

* cited by examiner

TRANSMISSION OF DATA TO EMERGENCY RESPONSE PERSONNEL

RELATED APPLICATION INFORMATION

This application is a continuation of U.S. application Ser. No. 13/079,440 filed Apr. 4, 2011, which is a continuation of U.S. application Ser. No. 11/856,618 filed Sep. 17, 2007 which is a continuation of U.S. application Ser. No. 10/863,668, filed Jun. 8, 2004, now U.S. Pat. No. 7,271,704 issued Sep. 18, 2007.

This application is also related to the following applications: U.S. application Ser. No. 10/614,948, filed Jul. 8, 2003, now U.S. Pat. No. 7,891,435 issued Feb. 22, 2011, and U.S. application Ser. No. 10/782,288, filed Feb. 19, 2004, now U.S. Pat. No. 7,174,769 issued Feb. 13, 2007, both of which are continuations-in-part of U.S. application Ser. No. 10/274,606, filed Oct. 21, 2002, now U.S. Pat. No. 7,188,679 issued Mar. 13, 2007, which is a continuation-in-part of U.S. application Ser. No. 09/832,531, filed Apr. 11, 2001, now U.S. Pat. No. 6,585,055, issued Jul. 1, 2003, which is a continuation-in-part of U.S. application Ser. No. 09/212,121, filed Dec. 15, 1998, now U.S. Pat. No. 6,302,218, issued Oct. 16, 2001, which is a continuation of U.S. application Ser. No. 08/879,445, filed Jun. 20, 1997, now U.S. Pat. No. 5,848,651, issued Dec. 15, 1998, which is a continuation-in-part of U.S. application Ser. No. 08/590,411, filed Jan. 23, 1996, now U.S. Pat. No. 5,775,430, issued Jul. 7, 1998, and a continuation-in-part of International Application No. PCT/US97/01025, with an International Filing Date of Jan. 23, 1997, now abandoned, the complete disclosures of all of which are incorporated herein by reference.

Each of the foregoing patents and applications is incorporated herein by reference in its entirety.

TECHNICAL FIELD

This description relates to transmission of data (e.g., temperature data, presence of an obstruction, etc.) sensed at a one or more emergency equipment stations in a network of emergency equipment stations to emergency response personnel.

BACKGROUND

A system includes a fire extinguisher station having a number of sensors to detect various predetermined conditions that can be communicated in alarms to a central station. The central station receives alarms from the fire extinguisher and determines whether to contact emergency personnel and/or building maintenance personnel. Other items of emergency equipment can be included in the system for improved detection and response to emergency conditions.

SUMMARY

In one aspect, the invention features a system for communicating information to emergency response personnel that includes one or more emergency equipment stations and a remote central station. Emergency equipment stations includes an emergency assistance device (e.g., fire extinguisher, fire pull alarm, defibrillator, emergency lighting, emergency egress lighting, etc.) and one or more sensors that sense one or more predetermined conditions (e.g., ambient air temperature, presence of an obstruction restricting access to the station, etc.). The stations are in communication with a remote central station that receives and transmits data indicating a sensed condition to a communications device associated with emergency response personnel.

In one particular implementation, an emergency equipment station is a fire extinguisher station which includes a fire extinguisher and one or more sensors configured to sense conditions such as ambient air temperature near the station, removal of the fire extinguisher from an installed position at the emergency equipment station, an out-of-range pressure condition of the fire extinguisher tank, and/or presence of an obstruction restricting access to the fire extinguisher at the emergency equipment station.

In another implementation, an emergency equipment station is a fire alarm pull station which includes a fire pull alarm and one or more sensors configured to sense conditions such as ambient air temperature near the station and/or presence of an obstruction restricting access to the fire pull alarm at the emergency equipment station.

In another implementation, an emergency equipment station is a defibrillator station which includes a defibrillator and one or more sensors configured to sense conditions such as ambient air temperature near the station, discharge of the defibrillator and/or presence of an obstruction restricting access to the defibrillator at the emergency equipment station.

In another implementation, an emergency equipment station is a emergency lighting station which includes emergency lighting and one or more sensors configured to sense conditions such as ambient air temperature near the station and/or presence of an obstruction restricting access to an area intended to be lit by the emergency lighting station.

In another implementation, an emergency equipment station is a emergency egress lighting which includes emergency egress lighting associated with an emergency exit way (e.g., an emergency door, window, etc.) and one or more sensors configured to sense conditions such as ambient air temperature near the station and/or presence of an obstruction restricting access to the emergency exit way associated with the emergency lighting station.

In some configurations, the central station is configured to generate and transmit a graphical map showing the location and sensed condition(s) to a communications device associated with emergency response personnel. For example, if the central station receives a signal from an emergency equipment station indicating the presence of an obstruction restricting access to the station (e.g., an obstruction to an emergency exit way associated with an emergency lighting station), the central station may generate and transmit a graphical map of the building showing the location of the blocked exit way. Similarly, if the emergency equipment stations are adapted to sense ambient air temperature and the central station receives a signal, e.g., from a smoke detector system, indicating a possible fire, the central station may generate and transmit a graphical temperature map of the building to emergency response personnel. In other configurations, the central station may transmit textual data (e.g., a table or chart) indicating the location and nature of the sensed condition(s) (e.g., a blocked emergency exit way on the fifth floor, north side).

In some configurations, the central station transmits data indicating a sensed condition to the emergency response personnel immediately upon receiving sensory data from an emergency equipment station. For example, if the emergency equipment station is a fire extinguisher station, and a sensor associated with the fire extinguisher station senses removal of the fire extinguisher from an installed position, the central station may be configured to transmit an signal to emergency response personnel immediately upon receiving a signal from the emergency equipment station indicating the removal of the fire extinguisher. In other configurations, the central station is configured to transmit data to emergency response personnel in response to receiving indication of an actual or suspected fire (e.g., receipt of a fire alarm signal from a smoke alarm system or a fire pull alarm station). For example, if an emergency equipment station is configured to sense ambient air temperature, data indicating the ambient air temperature near one or more stations may be transmitted to emergency response personnel when the central station receives a signal indicating the presence of a fire. A system of emergency equipment stations distributed throughout one or more buildings in which the emergency equipment stations are equipped with a sensor (e.g., a thermistor or thermocouple) for detecting ambient air temperature permits a central station to generate and transmit a continuously-updated temperature map of the building(s) to fire response personnel in the event of an actual or suspected fire. This gives emergency response personnel a real-time view of hot spots in the building and helps to identify locations of suspected fire.

In some configurations, the emergency equipment stations include circuitry (e.g., a wireless radio-frequency (RF) transmitter, network card, etc.) for transmitting data indicating sensed conditions to the remote central station. In these configurations, the central station has circuitry for receiving the data from the emergency equipment stations (e.g., an RF receiver, network card, etc.). The central station may also include transmission circuitry (e.g., modem, network card, RF transmitter, etc.) for transmitting data to emergency response personnel. The central station may transmit data to a communications device (e.g., computer with a modem, handheld computer with modem, etc.) located at a fire station, within an emergency response vehicle, and/or in a hand held device carried by an emergency response provider.

In another aspect, the invention features a method for communicating information to emergency response personnel that includes receiving data indicating ambient air temperature near a plurality of emergency equipment stations installed throughout one or more buildings, receiving data indicating a fire in one or more of the buildings, and in response to receiving data indicating a fire in the building(s), generating and transmitting a message indicating ambient air temperature near one or more selected emergency equipment station to a communications device associated with the emergency response personnel.

In some configurations, generation of a message includes generating a graphical temperature map of all or part of the building(s) using the data indicating ambient air temperature near one or more of the selected emergency equipment stations and incorporating the graphical temperature map in the message. In other configurations, generation of a messages includes generating a text file (e.g., a table or chart) using the data indicating ambient air temperature near one or more selected emergency equipment stations and incorporating the text file in the message. Transmission of the message may be accomplished using a computer network (e.g., the Internet), cellular network, satellite network, and/or the public switched telephone network.

In another aspect the invention features a method for communicating information to emergency response personnel that includes providing a system of emergency equipment stations installed throughout one or more buildings, wherein at least some of the emergency equipment stations are configured to sense the presence of an obstruction restricting access to the emergency equipment station and, in response to sensing presence of an obstruction, generate a signal indicating the presence of an obstruction restricting access to the emergency equipment station. The method also includes monitoring the system of emergency equipment stations (e.g., with a remote central station), and in response to receiving a signal indicating the presence of an obstruction, generating a message indicating the presence of an obstruction restricting access to the emergency equipment station at which the obstruction was sensed.

In some configurations, generation of a message includes generating a graphical map of all or part of the one or more buildings showing the location of the emergency equipment station at which the presence of an obstruction was sensed. In other configurations, generation of a message includes generating a text file showing the location of the emergency equipment station which sensed the presence of an obstruction and incorporating the text file in the message. Transmission of the message may be accomplished using a computer network (e.g., the Internet), cellular network, satellite network, and/or the public switched telephone network.

In another aspect, the invention features an emergency equipment station that includes an emergency assistance device (e.g., a fire extinguisher, fire pull alarm, defibrillator, emergency lighting, emergency egress lighting, etc.), a first sensor configured to sense ambient air temperature near the emergency equipment station and an electronic circuit in communication between the first sensor and a remote central station for issue of a signal to the remote central station indicating a sensed ambient air temperature.

In some configurations, the emergency equipment station includes additional sensors for detecting predetermined internal and external conditions such an out-of-range pressure condition of a fire extinguisher tank, presence of an obstruction restricting access to the station, discharge of the defibrillator, etc.

In some configurations, the emergency equipment station is configured to automatically (i.e., without instruction from an external source) issue a signal to the remote central station indicating sensed ambient air temperature. In some configurations, the emergency equipment station is configured to issue a signal to the remote central station in response to a request from the remote central station.

In some configurations, the emergency equipment station is configured to continuously issue a signal to the remote central station indicating sensed ambient air temperature. In other configurations, the emergency equipment station is configured to periodically (e.g. every 30 seconds) issue a signal to the remote central station indicating sensed ambient air temperature.

In some configurations, the remote central station is a computer that receives and/or transmits data to/from the emergency equipment station using a wireless and/or hard-wired communications network.

The details of several implementations of various aspects of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
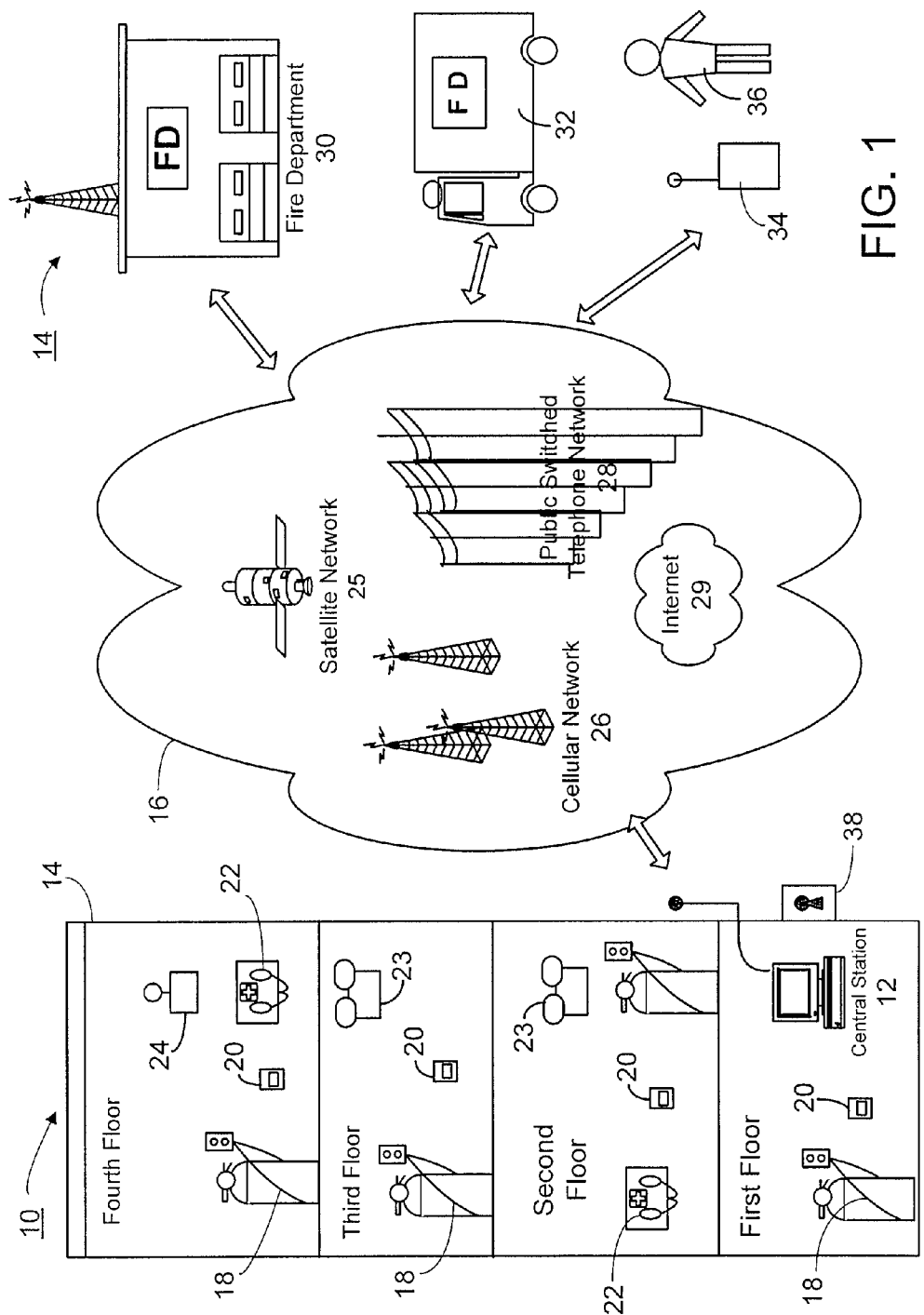
FIG. 1 is a diagram of a system for communicating information collected at a network of emergency equipment stations to emergency response personnel.

Referring to FIG. 1, a system 10 for remote monitoring of emergency equipment is distributed throughout (e.g., in rooms, hallways, etc.) a healthcare facility (e.g., a hospital, assisted living facility, a nursing home, etc.), a commercial facility (e.g., a shopping mall, restaurant, dance club, gymnasium, etc.), an educational institution (e.g., a college campus, dormitory, etc.), a residence (e.g., a residential home, residential development, apartment complex, condominium complex, etc.), or other facility (e.g., an airport, train station, bus station, etc.). In this particular example, emergency equipment stations are distributed throughout four floors of a building 14. As will be explained in more detail below, each emergency equipment station includes an emergency assistance device (e.g., a fire extinguisher, fire pull alarm, emergency egress lighting, emergency lighting, defibrillator, etc.) and one or more sensors adapted to sense various internal and external conditions (e.g., ambient air temperature, presence of an obstruction blocking access to emergency assistance device, etc.).

System 10 includes remote central station 12 located in building 14 that is in communication with emergency response personnel 14 via a communication medium 16 such as a satellite network 24, cellular network 26, public switched telephone network (PSTN) 28, or a computer network such as the Internet 29. Remote central station 12 remotely monitors a network of emergency equipment stations, e.g., fire extinguisher stations 18, fire alarm pull stations 20, defibrillator stations 22, emergency lighting stations 23, and emergency egress station 24, for assistance of building occupants during an emergency. Each emergency equipment station includes sensors and circuitry for monitoring internal and/or external conditions such as ambient air temperature, presence of an obstruction in front of the equipment, removal of the equipment from an installed position, etc.

Upon detection of an alarm (e.g., a fire alarm), remote central station 12 is configured to relay information about monitored internal and/or external conditions to emergency response personnel. For example, if ambient temperature is a condition monitored by the network of emergency equipment, remote central station 12 may be configured to transmit temperature data to emergency response personnel when a fire alarm is triggered. By receiving this data, emergency response personnel (e.g., the fire department) can be provided with a temperature map of each floor of the building 14 thus helping to pinpoint locations of suspected fires.

Emergency response personnel 14 may receive data transmitted by the remote central station in several ways. For example, data transmitted by remote central station 12 may received by a communications device (e.g., dial up modem, cable modem, cellular modem, computer network interface card, etc.) at a computer at a fire station 30, a computer installed within an emergency response vehicle 32 (e.g., a fire truck or rescue squad), and/or a hand held device 34 (e.g., a tablet computer, personal data assistant, cellular device) carried by emergency response personnel 36.

Remote central station 12 is also configured to receive signals from emergency response personnel. For example, in this embodiment, remote central station 12 is configured to receive a signal to open lock box 38 that allows emergency response personnel to access the building.

Figure 2:
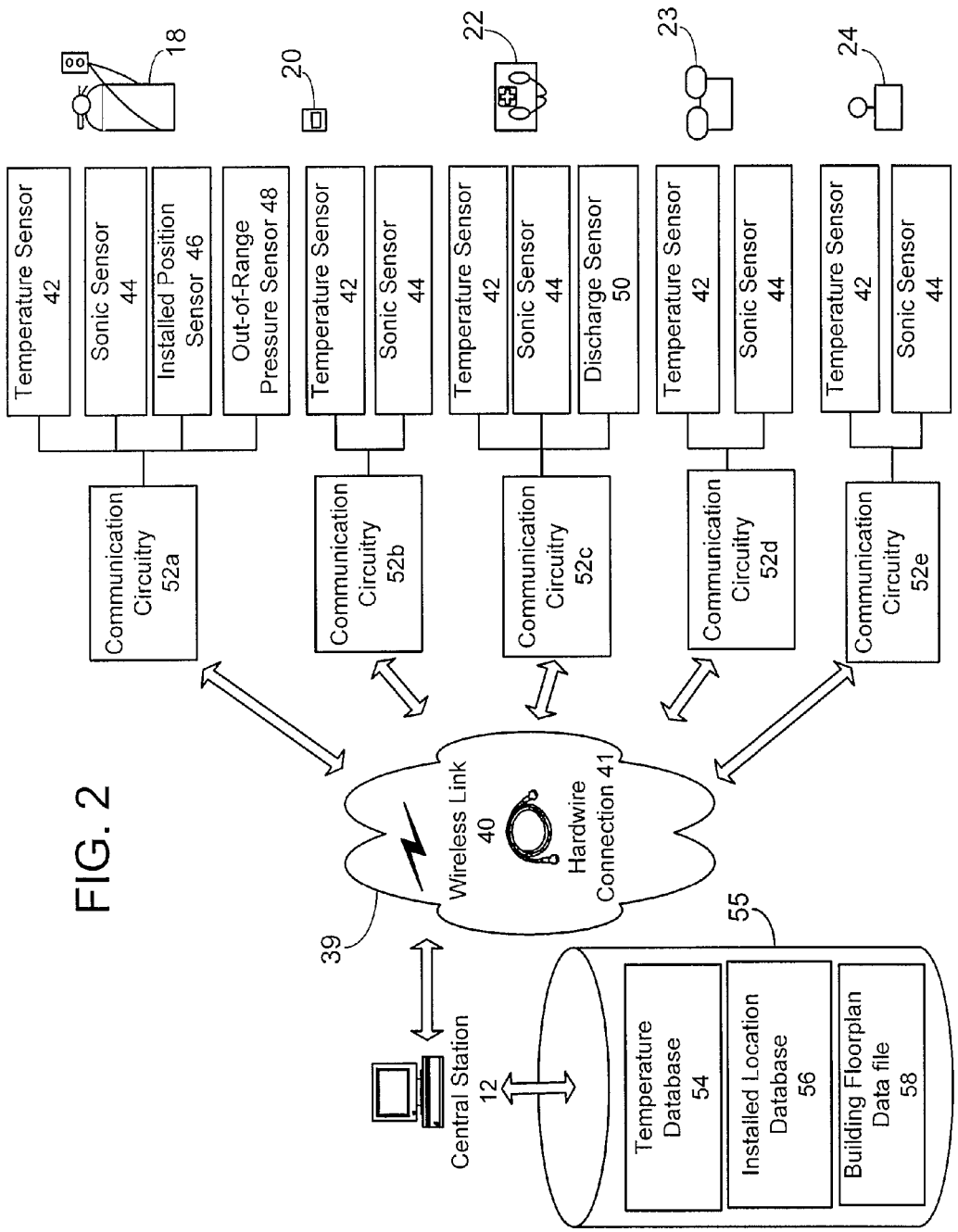
FIG. 2 is a diagram of a system for collecting information sensed at various emergency equipment stations.

As shown in FIG. 2, each emergency equipment station, e.g. fire extinguisher station 18, fire alarm pull station 20, defibrillator station 22, emergency lighting station 23 and emergency egress station 24, monitors various internal and/or external conditions and is in communication with the remote central station 12 over a communications link 39 such as wireless link 40, hardwire connection 41 or a combination thereof. In an implementation using a wireless communications link between remote central station 12 and an emergency equipment station, a wireless repeater mesh network may be employed to relay a signal transmitted from an emergency equipment station to the remote central station.

In the implementation shown in FIG. 2, each emergency equipment station includes a temperature sensor 42 for detecting ambient air temperature near the equipment and an ultrasonic sensor 44 for detecting the presence of an obstruction affecting access to the equipment. Temperature sensor 42 may employ any known suitable temperature sensing device such as a thermocouple or thermistor. In addition to these sensors, fire extinguisher station 18 may also include an installed position sensor 46 to determine if the extinguisher has been removed from its installed position and an out-of-range pressure sensor 48 to detect when the pressure of fluid contained in the extinguisher is outside a predetermined pressure range. Each defibrillators station 20 includes a discharge sensor 50 for detecting when the defibrillator is discharged.

Each sensor associated with each emergency equipment station is in communication with communication circuitry 52a-52e. In this implementation, communications circuitry 52a-52e is configured for one-way communication from the emergency equipment station to remote central station 12. In particular, communication circuitry 52a-52e is configured to continuously transmit a signal indicating the current ambient temperature to the remote central server, where it is stored in database 54 or other similar structure (e.g., a data file) in storage device 55 (e.g., hard drive, CD-ROM, etc.) in communication with remote central station 12. Additionally, the installed location of each emergency equipment station is stored in database 56 and the building floor plan is stored in data file 58 in storage device 55 in communication with remote central station 12. By providing data indicating the current temperature of the emergency equipment stations, the location of the emergency equipment stations, and the building floor plan, remote central station 12 is able to assemble a graphical temperature map of the building, which may be transmitted to emergency response personnel when an alarm indicating a fire is triggered. In other embodiments, the ambient air temperature may be transmitted periodically (e.g., every 30 seconds) to remote central station 12.

Communication circuitry 52a-52e is also configured to initiate and transmit an alarm signal to remote central station 12 upon detection of a predetermined condition by one of the sensors. For example, if sonic sensor 44 detects the presence of an object obstructing access to an emergency equipment station, associated communications circuitry will initiate and transmit an alarm signal to the remote central station indicating obstruction of a particular emergency equipment station. Similarly, if installed position sensor 46 detects that a fire extinguisher has been removed from its installed position or if out-of-range pressure sensor 48 detects that the internal pressure of the extinguisher is out of range (e.g., fallen below or risen above a predetermined pressure), the associated communication circuitry, e.g., communication circuitry 52a, will initiate and transmit an alarm signal to the remote central station indicating a removal of the particular fire extinguisher from its installed position or an out-of-range pressure condition. Likewise, if discharge sensor 50 associated with the defibrillator station 22 detects that the defibrillator has been discharged, the associated communications circuitry, e.g., communication circuitry 52c, will initiate and transmit an alarm signal to remote central station 12 indicating discharge of a particular defibrillator.

Remote central station 12 is configured to associate a received signal with a particular emergency equipment station. In this regard, the various signals transmitted by the emergency equipment stations (e.g., temperature signals, out-of-range pressure signals, etc.) include an identification code (e.g., an Internet Protocol address) or other information uniquely identifying the transmitting emergency equipment station. Installed location database 56 includes data correlating the type of emergency equipment station (e.g., fire extinguisher station, defibrillator station, etc.) and the location of each station (e.g., room 407 on the fourth floor) with each station identification code. In another implementation, each emergency equipment stations is configured to transmit signals to the remote central station via a radio frequency (RF) signal tuned to a unique frequency, thus allowing the remote central station to identify the source of the signal by the frequency of the received signal.

In another implementation, communications circuitry associated with emergency equipment station is configured for two-way communication between remote central station 12 and the respective station. In this implementation, the communication circuitry associated with each emergency equipment station is configured to receive requests for data from the remote central station. For example, the remote central station may request one or more emergency equipment stations to transmit the status of monitored internal and/or external conditions (e.g., current ambient air temperature, status of pressure of fluid in a fire extinguisher tank, etc.). In this implementation, ambient air temperature may not be continuously transmitted to the remote central stations, but may only be transmitted when data is requested by the remote central station. In one particular implementation, data (e.g., ambient air temperature data, alarm signals indicating occurrence of a sensed condition, etc.) is communicated via a network connection (e.g., a wireless or hardwire Ethernet connection) established between remote central station 12 and each respective emergency equipment station in the network of emergency equipment stations.

Figure 3:
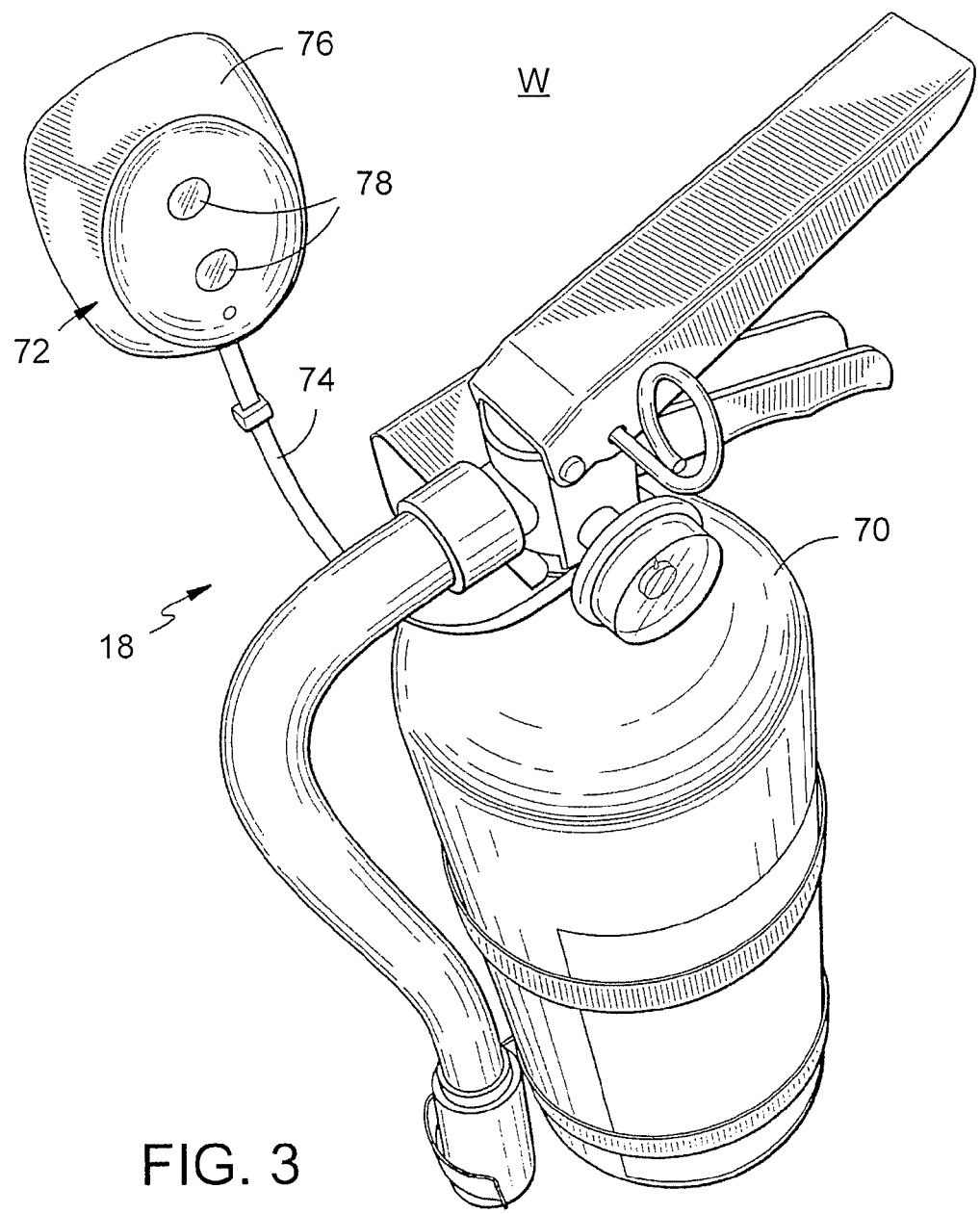
FIGS. 3-5 are each a perspective view of a fire extinguisher station.
Figure 4:
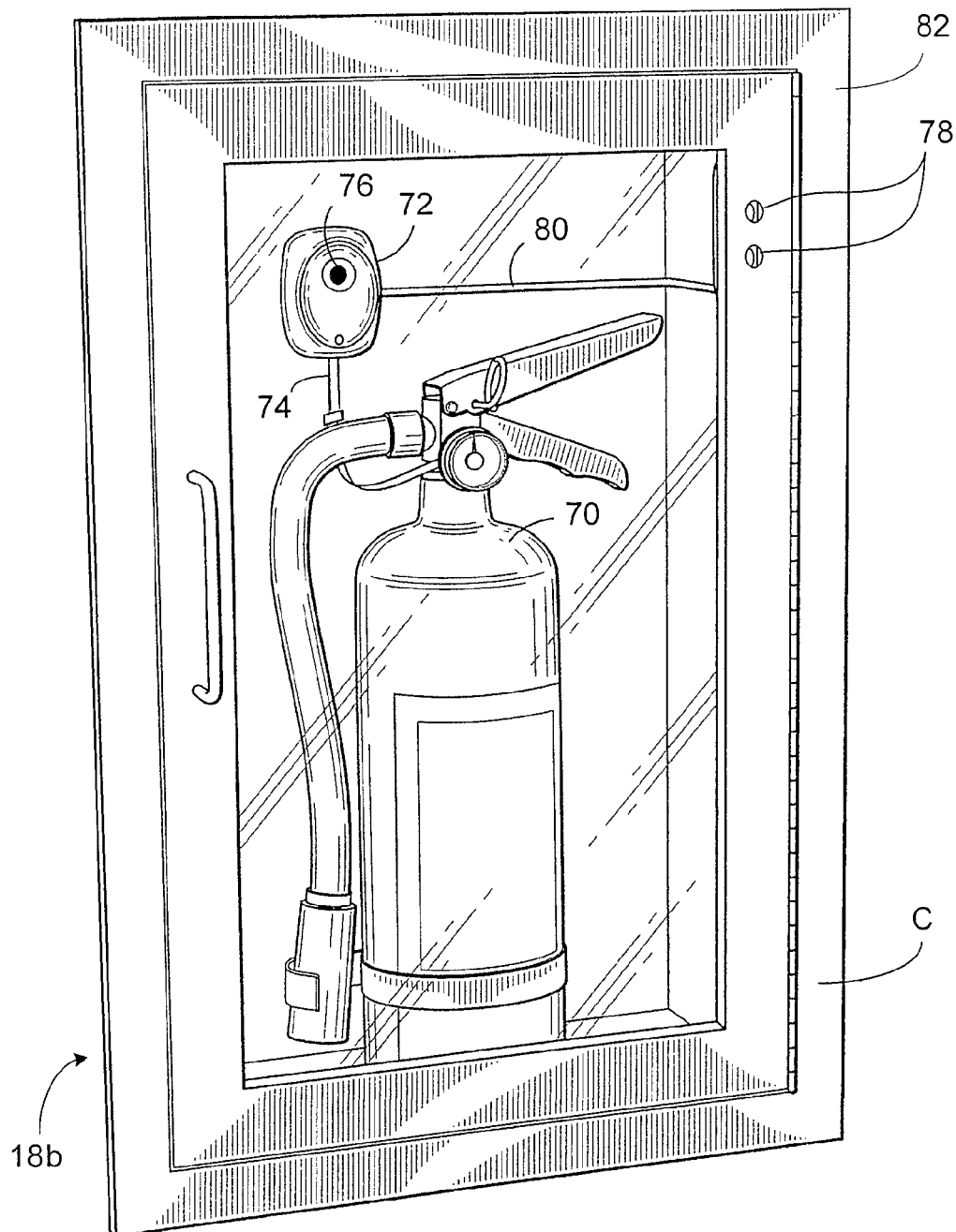

As an example of an emergency equipment station, a fire extinguisher station 18 shown in FIG. 3 includes a portable fire extinguisher 70 mounted to a wall, post, or other support surface, W, and in FIG. 4, another portable fire extinguisher station 18b includes an extinguisher 70 mounted within a wall box or cabinet, C. In these embodiments, the fire extinguisher 70 at each fire extinguisher station 18, 18b is releasably connected to a docking station 72 by an electronics and communications tether 74 to provide releasable engagement for electronics and/or communications connection between docking station 72 and portable fire extinguisher(s) 70 at each station 18a, 18b. Typically signals issued from or to fire extinguisher 70 are transmitted over the electronics and communication tether 74. For example, a signal, initiated by one or more Hall Effect sensors included in fire extinguisher 70, which is indicative of out-of-range (low or high) pressure of the fire extinguishing material contained within the tank volume, is transmitted from fire extinguisher 70 across tether 74 to docking station 72 and then to remote central station 12 (shown in FIGS. 1-2).

In the embodiment shown in FIG. 3, docking station 72 is fixedly mounted to the wall, W, at a predetermined position spaced generally above fire extinguisher 70. Docking station 72 consists of housing 76 containing sonic sensor 44 (shown in FIG. 2) and defining spaced apertures or windows 78 through which the sonic sensor emits and receives ultrasonic signals. In the embodiment of FIG. 4, where docking station 72 is disposed with a wall cabinet, C, the sonic sensor is connected, e.g., by cable 80, to apertures or windows in the outer surface of cabinet door 82 for emitting and receiving the ultrasonic signals.

Also, disposed within docking station housing 72 is temperature sensor 42 (shown in FIG. 2) that senses the ambient air temperature and communications circuitry 52 (shown in FIG. 2) for transmitting signals to remote central station 12.

Extending generally from the base of docking station housing 72 is electronics and communications tether 74 received by a connector in communication with a valve monitoring internal content pressure of the fire extinguisher. The length of tether 74, and the tenacity of engagement of the connection between the connector and the tether, are preferably selected so that any significant movement of fire extinguisher 70 relative to its installed position, i.e., the position in which it is placed at installation by a fire extinguisher professional, whether removal, or, in a preferred embodiment, merely upon rotation with movement in excess of a predetermined threshold value, will result in dislodgement of tether 74 from the connector, initiating a signal to remote central station 12, as discussed above.

Docking station 76 may be powered by alternating current, e.g., by a hardwire connection into a facility's electrical supply, or it may be powered by direct current, e.g., by a battery within docking station housing 76. If powered by alternating current, an auxiliary power supply, e.g., in the form of a battery, may be provided in case of power outage.

Figure 5:
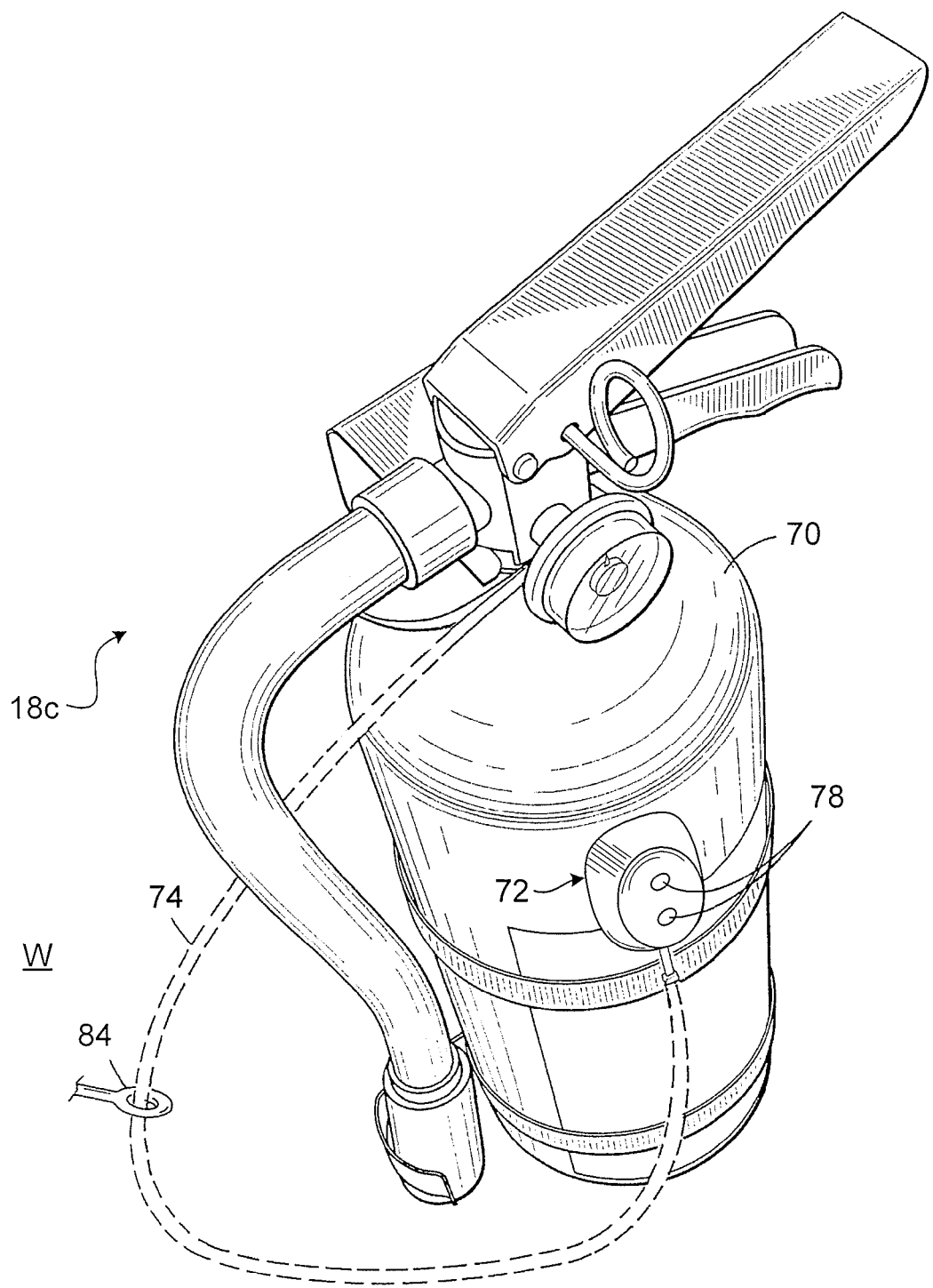

Referring to FIG. 5, in another embodiment of portable fire extinguisher station 18c, components of docking station 72, as described above, may instead be mounted to fire extinguisher 70, e.g., within housing 76, thereby allowing the fire extinguisher to be located, if desired, without wall mounting or enclosure. In the embodiment shown, housing 76 contains temperature sensor 43 and sonic sensor 44 (both shown in FIG. 2). Housing 76 also defines apertures or windows 78 for detecting obstructions as previously mentioned. Communications circuitry 52 is also disposed within housing 76, for communication of signals, e.g., wireless signals, between fire extinguisher station 18c and remote central station 12.

An electronics and communication tether 74 may extend between connections to housing 76 and fire extinguisher 70, as indicated in dashed line, e.g., engaged through an aperture of I-bolt 84 anchored into a wall W, such that any significant movement of fire extinguisher 70 relative to its position at rest, in excess of a predetermined threshold value, results in disengagement of the tether 74 from connection with extinguisher 70, thereby to initiate a wireless signal to remote central station 12. In another embodiment (not shown), a tether or leash, e.g. in the form of a cord, wire, rope or the like, may extend from a first end secured, e.g., to a wall, to engagement of its second end in a socket defined, e.g., by housing 76, whereby dislodgement of the tether or leash from the socket initiates a wireless signal.

Communication circuitry 52 (shown in FIG. 2) is located within housing 74 to communicate by, for example, wireless signal between fire extinguisher station 18 and remote central station 12. Signals indicating the current ambient temperature are continuously communicated between remote central station 12 and fire extinguisher station 18. Additionally, upon detection of a monitored internal or external condition such as an out-of-range pressure condition, removal of an extinguisher from its installed position, or detection of an obstruction in front of station 18, a signal indicating the occurrence of the condition is transmitted (e.g., via a wireless or hardwire transmission) to remote central station 12. In this manner, a system of emergency equipment stations (e.g., fire extinguisher stations), distributed over a considerable area, are maintained in communication with remote central station 12.

Figure 6:
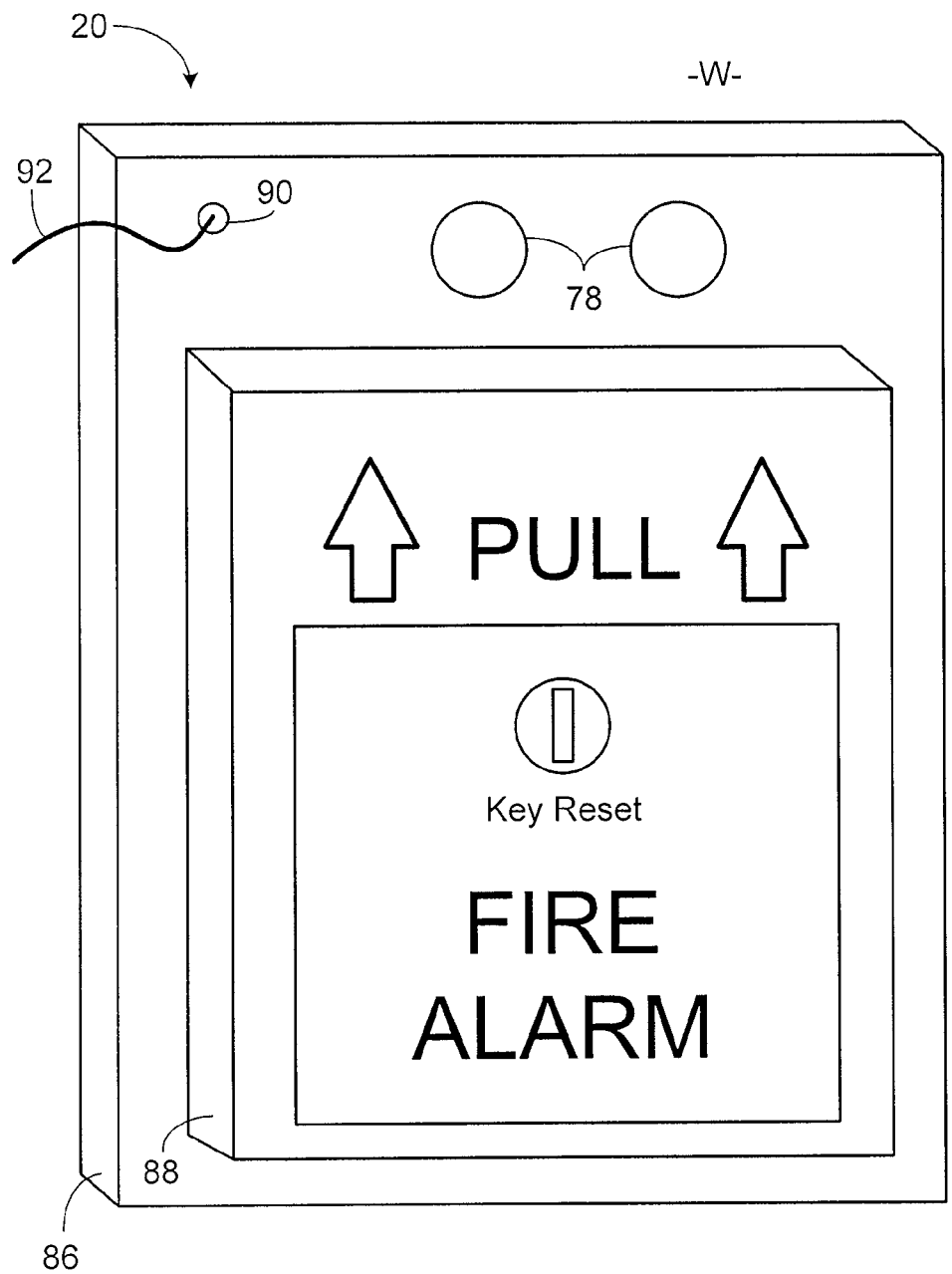
FIGS. 6-7 are perspective views of fire alarm pull stations.

Referring to FIG. 6, in another emergency equipment station, namely fire alarm pull station 22, components of docking station 72, as described above, are included in housing 86 that is shown mounted to a wall, post, or other support surface, W, and receives pull alarm 88. In the embodiment shown, housing 86 contains temperature sensor 42, sonic sensor 44, and communications circuitry 52 (all shown in FIG. 2). Housing 86 also defines apertures or windows 78 for emitting and receiving ultrasonic signals to detect one or more objects that obstruct viewing of and access to fire alarm pull station 20. Additionally, if pull alarm 88 is pulled by a passerby in the event of an emergency to sound a fire alarm, a signal is issued by pull station 20 and transmitted to remote central station 12. In other implementations, fire alarm pull station 20 may initiate other signals based on other internal conditions associated within the pull station. For example, a signal may be initiated if a battery included in fire alarm pull station 20 needs to be replaced or recharged.

The temperature sensor continuously transmits a signal to remote central station 12 indicating the ambient air temperature near the fire alarm pull station 20. Additionally, the sonic sensor initiates a signal to indicate an obstruction that may be restricting visibility of or access to fire alarm pull station 20. To initiate these signals, communications circuitry 52 is also disposed within housing 86 for transmitting signals to remote central station 12. To transmit a signal, communications circuitry 52 sends the signal via a hardwire connection or a wireless link from housing 86 to remote central station 12. To provide a hardwire connection, in this embodiment, housing 86 includes connection terminal 90 for connecting to hardwire connection 92 for transmitting signals to and receiving signals from remote central station 12. In other embodiments a wireless link is established between housing 86 and remote central station 12 for transmitting and receiving signals. For example, communication circuitry 52 included within housing 86 may include an RF transmitter and antenna for transmission of RF signals to remote central station 12. Also, in some embodiments communication circuitry 52 is capable of receiving wireless signals from remote central station 12, other wireless devices (e.g. cellular telephone, etc.), or from one or more other emergency equipment stations for relaying signals in a networking scheme. By forming a network (e.g., a local area network, wide area network, or similar) with hardwire connections or wireless links, or a combination of hardwire connections and wireless links, a system of emergency equipment stations, distributed over a considerable area, is capable of being remotely monitored by remote central station 12. Additionally, in some embodiments, housing 86 includes communications circuitry 52 configured to transmit signals via a hardwire connection and a wireless link, thus providing redundant transmission pathways between remote central station 12 and housing 86. Some or all of the information received by remote central station 12 may be forwarded to emergency response personnel to assist in responding to an emergency situation.

Along with transmitting internal conditions (e.g., battery replacement or recharging, etc.) and external conditions (e.g., ambient air temperature, detection of an obstruction, etc.) associated with fire alarm pull station 20, in some embodiments housing 86 of the fire alarm pull station also provides local indications that the pull station has been operated, e.g., in the event of an emergency. For example, housing 86 can include or be in communication with an audible signaling device (e.g., a speaker) for emitting an audible tone or signal (e.g., verbal commands) to alert people in the local vicinity to a detected obstruction of the pull station or other external condition such as the operation of the pull station by a passerby due to fire. The audible signal may also consist of a recorded information message, e.g., instructions for evacuation or for assisting personnel located near fire alarm pull station 20. Also, housing 86 may include one or more alert lights, strobes, or other similar lighting devices that are driven by circuitry included in housing 86 such that the alert lights illuminate, flash, or strobe for visually alerting personnel in the vicinity that access to and view of fire alarm pull station 20 is obstructed, or that pull station 20 has been actuated.

Figure 7:
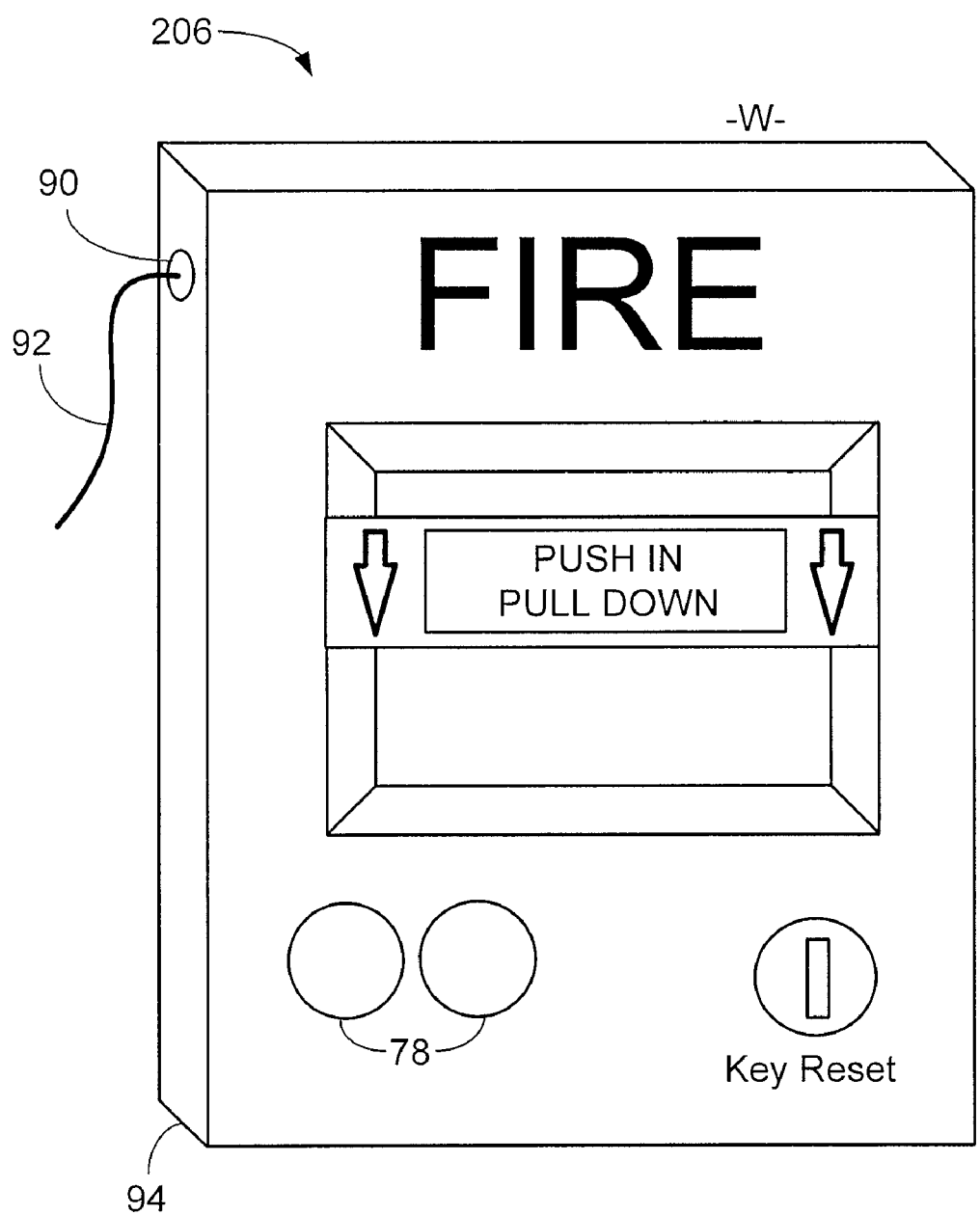

Referring to FIG. 7, in another embodiment of fire alarm pull station 20b, components of docking station 72, as described above, are included within the housing of pull alarm 94, rather than in a separate housing that receives the pull alarm as shown in FIG. 6. In the embodiment of FIG. 7, fire alarm pull station 20b includes communications circuitry 52, temperature sensor 42, sonic sensor 44 (all shown in FIG. 2) and defines the apertures or windows 78 for emitting and receiving ultrasonic signals for detecting obstructions at ranges, e.g., from about 6 inches to about 10 feet dependent, upon the environment. Including the temperature sensor and sonic sensor, along with communication circuitry 52 within fire alarm pull station 20b, permits pull station 20b of being located on a wall, post, or other support surface, W, in a relatively smaller area that might otherwise be ill-suited for supporting the relatively larger housing 86 shown in FIG. 6.

Additionally, by including the temperature sensor within the fire alarm pull station, a signal can be continuously transmitted to remote central station 12 to indicate current ambient air temperature near the fire alarm pull station. Similarly, by including the sonic sensor in a fire alarm pull station, along with apertures or windows 92, obstructions to visibility and accessibility of the pull station can be detected by the sonar module for issue of a signal is issued by electronic and communication circuitry 94 to remote central station 12. Also, similar to housing 86, in this embodiment, fire alarm pull station 94 includes connection terminal 90 for connecting hardwire connection 92 to the pull station for transmitting signals to remote central station 12. Alternatively, or in concert with hardwire connection 92, communications circuitry 52 within fire alarm pull station 94 may include a wireless transmitter and/or a transreceiver and antenna for transmitting and/or receiving wireless signals to/from remote central station 12 and provide capability for distribution of a system of fire alarm pull stations over a considerable area while maintaining wireless communication between each fire alarm pull station and remote central station 12. Additionally, in some embodiments, fire alarm pull station 94 includes an audible signaling device (e.g., a speaker) and/or alert lights for issuing an alert to nearby personnel or passersby that the pull station is, e.g., being obstructed.

Figure 8:
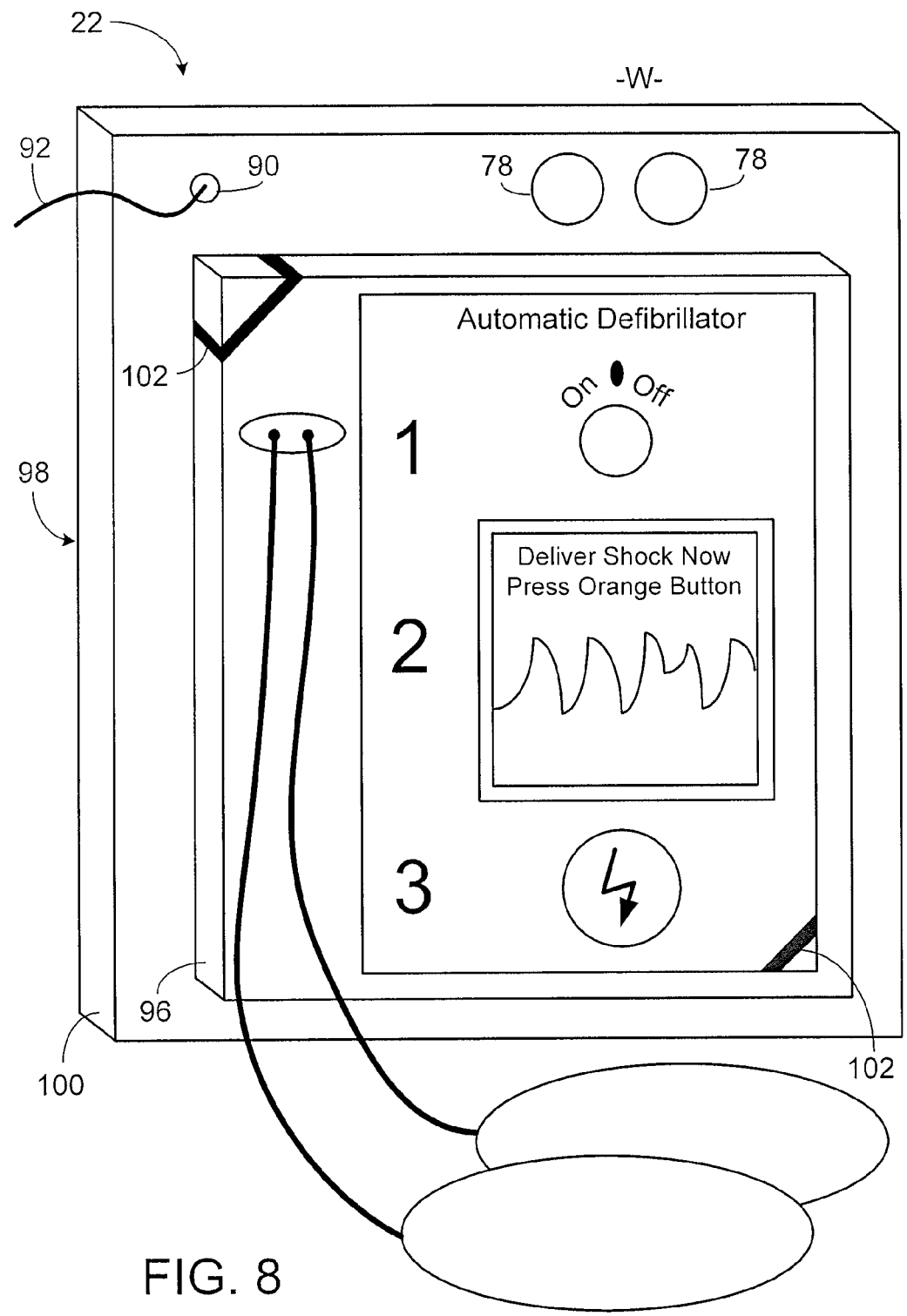
FIG. 8 is a perspective view of a defibrillator station.

Referring to FIG. 8, another emergency equipment station, namely defibrillator station 22, includes defibrillator 96 attached to docking station 98 by one or more mechanical fasteners 102 (e.g., a clips, fastening material, etc.). Typically, defibrillator station 22 is mounted to a wall, post, or other support surface, W, so that defibrillator 96 is accessible by trained personnel or the general public for use during an emergency, e.g., such as a person suffering from sudden cardiac arrest or other life-threatening aliment. By distributing a system of defibrillator stations, for example, throughout an airport, shopping center, or other facility accessible by the public, in the event of an emergency, a defibrillator can be removed from a relatively nearby defibrillator station to provide assistance.

Docking station 98 includes housing 100 containing temperature sensor 42 for sensing ambient air temperature near the defibrillator station, sonic sensor 44 and apertures or windows 78 for detecting the presence of an obstruction restricting access to the defibrillator, discharge sensor 50 for detecting when defibrillator 96 has delivered a shock, and communication circuitry 52c (shown in FIG. 2) for transmitting signals indicating various monitored internal and external conditions.

Similar to the fire extinguisher stations, e.g., station 18 shown in FIG. 3, communications circuitry 52c continuously transmits to remote central station 12 a signal indicating ambient air temperature near defibrillator station 22. Additionally, upon detection of an obstruction by the sonic sensor or detection that the defibrillator has been discharged by the discharge sensor, communications circuitry 52c initiates and transmits a signal to remote central station 12, which identifies the defibrillator station and the sensed condition (e.g., presence of an obstruction or defibrillator discharge). Signals indicating monitored predetermined internal and external conditions are transmitted in this embodiment to remote central station 12 via hardwire connection 92 connected to terminal 90. However, in other embodiments, signals may be transmitted via a wireless link in lieu of or in addition to a hardwire connection.

Additionally, in some embodiments, other internal and/or external conditions may be sensed by defibrillator station 22 and communicated to remote central station 12. For example, if the defibrillator is removed from the docking station (e.g., in the event of an emergency), or if an internal battery needs attention (e.g., replacing, recharging, etc.), a signal is transmitted to the remote central station over the hardwire connection and/or in a wireless signal from an antenna.

Along with providing a signal to remote central station 12 indicating internal and/or external conditions of defibrillator 92 and/or defibrillator station 22, in some embodiments the defibrillator station includes an audible signaling device (e.g., a speaker) that issues an audible tone, signal, or message for alerting personnel and/or the general public to one or more of predetermined internal and external conditions. For example, if defibrillator station 92 is obstructed, or if defibrillator 92 is removed from the defibrillator station, an audible tone may be emitted by the audible signaling device. Also, defibrillator station 22 may include one or more alert lights, strobes, or other similar lighting devices for similarly alerting personnel and/or the general public to the one or more of the predetermined internal or external conditions associated with the defibrillator station or defibrillator 92.

Figure 9:
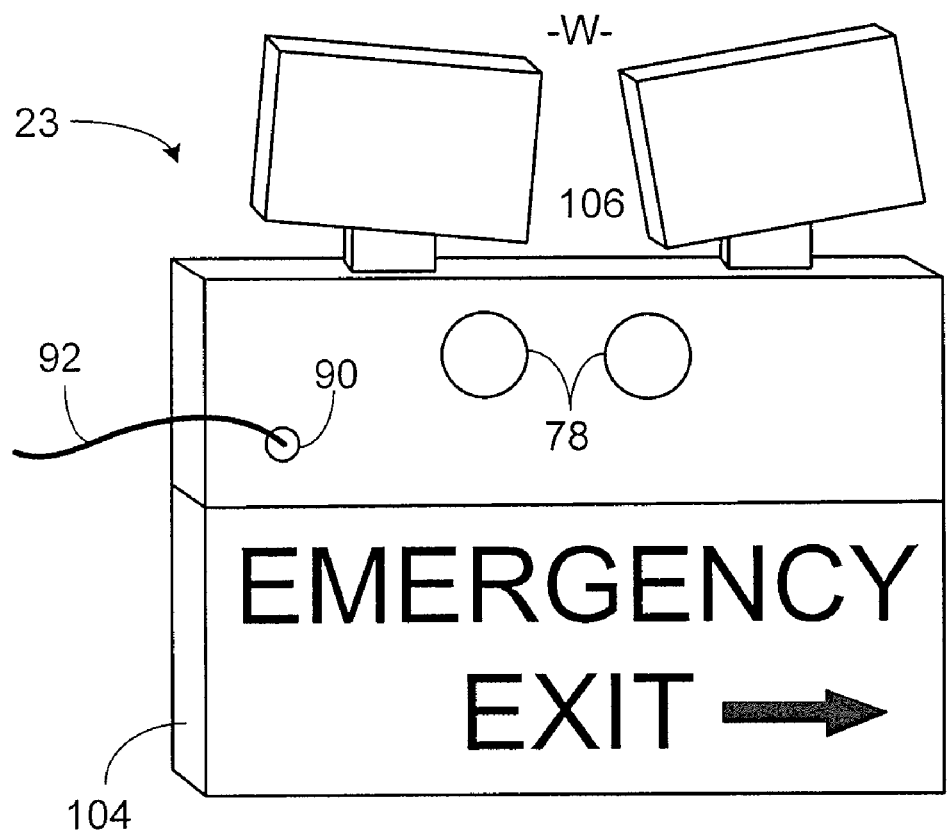
FIG. 9 is a perspective view of an emergency lighting station.

Referring to FIG. 9, another emergency equipment station, namely an emergency lighting station 23, includes housing 104 and a pair of emergency lights 106 that provide illumination in the event of an emergency (e.g., a fire, a power outage, etc.). In some embodiments, activation of emergency lights 106 is controlled remotely, e.g., from remote central station 12, or controlled locally by circuitry and sensors (e.g., a smoke detector) included in housing 104 or positioned in a nearby location (e.g., mounted in a ceiling). Typically, emergency lighting station 23 is mounted to a wall, post, or other support surface (e.g., a ceiling, doorway, etc.), W, for illuminating the local area during an emergency. In some embodiments, a system of emergency lighting stations is distributed throughout a commercial, industrial, educational, or other similar type of facility to provide emergency lighting. Additionally, in this embodiment, emergency lighting station 23 includes an "EMERGENCY EXIT" signal, which may or may not illuminate while directing people to an appropriate egress point (e.g., doorway) during an emergency.

Similar to previously mentioned embodiments, housing 104 of emergency lighting station 23 contains temperature sensor 42 for monitoring the ambient temperature near the emergency lighting station.

Housing 104 also includes sonic sensor 44 (shown in FIG. 2) and apertures or windows 78 for detecting obstructions. By including the sonic sensor within emergency lighting station 23, obstructions to operation of the emergency lighting station, i.e., illumination of the area intended to be illuminated, are detectable by the sonar module and a signal is initiated from communications circuitry 52 also included in the station. Similar to previously mentioned embodiments, emergency lighting station 23 includes connection terminal 90 that connects to hardwire connection 92 for transmitting signals to remote central station 12. In some embodiments the emergency lighting station includes wireless communication circuitry and an antenna in lieu of or in addition to a hardwire connection for providing wireless transmission of the signal to remote central station 12. Additionally, in some embodiments, the communication circuitry includes circuitry for transmitting both wireless signals over an antenna and hardwire signals via the hardwire connection for redundancy to provide a back-up signal transmission pathway.

As in other emergency equipment stations described above, communications circuitry 52 (shown in FIG. 2) is configured to continuously transmit a signal indicating the ambient air temperature to remote central station 12. In addition, communications circuitry 52 is configured to initiate a signal sent from emergency lighting station 24 to remote central station 12 upon the detection of one or more of the predetermined external conditions associated with the station, such as an obstruction detected by the sonar module through apertures or windows 78. In other embodiments, the communications circuitry may be configured to initiate a signal to remote central station 12 upon detection of a predetermined internal conditions associated with station 23 such as a battery back-up needing replacement or recharging, or an emergency lights 106 needing replacement. Additionally, emergency lighting station 23 may include an audible signaling device (e.g., a speaker) for emitting an audible tone, signal, or message to alert facility personnel and/or the general public in the vicinity that the station is currently obstructed or that another predetermined internal or external condition has occurred. Also, emergency lighting station 23 may include one or more alert lights, strobes, or other similar lighting devices, in addition to emergency lights 106, for emitting a visual alert to indicate, e.g., that the emergency lighting station is obstructed.

Figure 10:
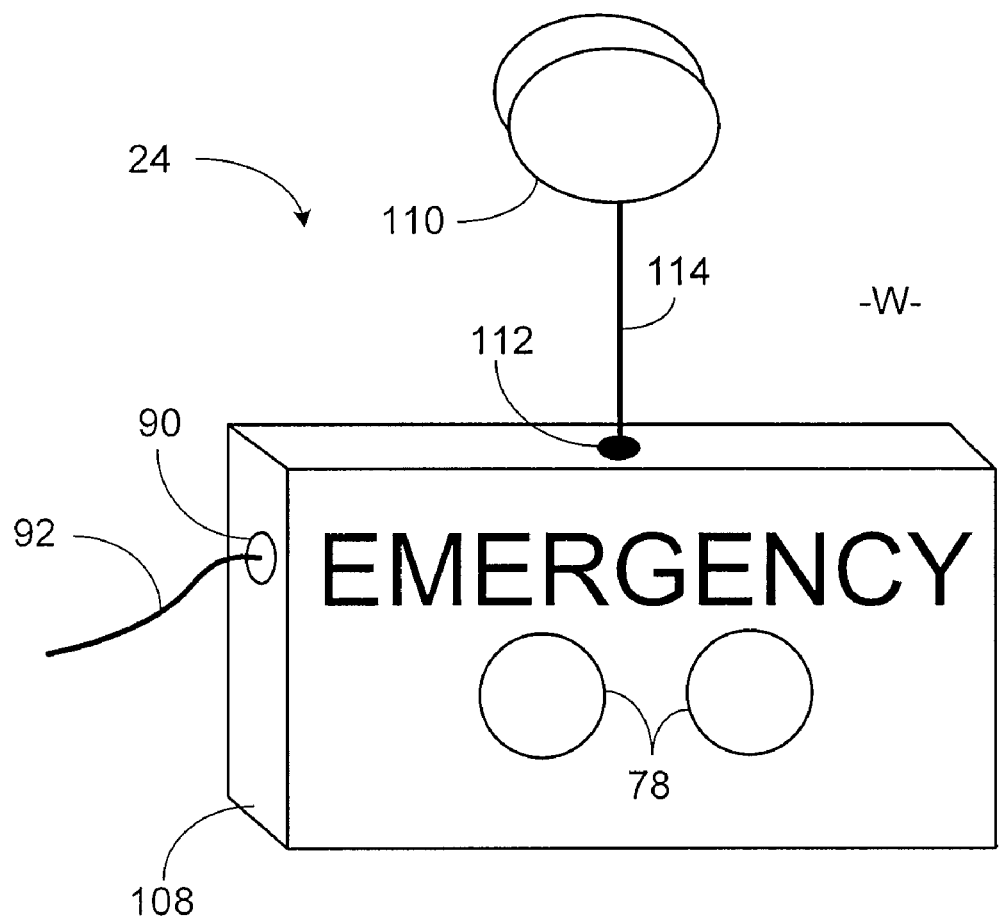
FIG. 10 is a perspective view of an emergency egress station.

Referring to FIG. 10, in another emergency equipment station, namely emergency egress station 24, includes housing 108 that is in communication with, e.g., strobe 110 providing illumination in the event of an emergency (e.g., a fire, a power outage, etc.). In some embodiments, activation of strobe 110 is controlled remotely, e.g., from remote central station 12, or controlled locally by circuitry and sensors (e.g., a smoke detector) included in emergency egress station 24 or positioned in a nearby location (e.g., mounted in a ceiling). Typically, emergency egress station 24 is mounted to a wall, post, or other support surface (e.g., a ceiling, doorway, etc.), W, for illuminating the local area during an emergency. Furthermore, in some embodiments, emergency egress station 24 is mounted on the support surface approximately slightly above floor level, such that a person crawling along the floor in the event of an emergency (e.g., fire) can detect the illuminating strobe for directing to an appropriate egress point, such as an emergency exit doorway.

Similar to previously mentioned embodiments, housing 108 of emergency egress station 24 contains temperature sensor module 42 (shown in FIG. 2) for detecting ambient air temperature near the station. Housing 108 also contains sonar module 44 and defines apertures or windows 78 for detecting obstructions. By including sonar module 44 within housing 108, obstructions to operation of emergency egress station 24, e.g., an emergency exit way (door, window, etc.) associated with the emergency egress station, are detectable by the sonar module and a signal is initiated from communications circuitry 52 also included in the housing. Similar to previously mentioned embodiments, emergency egress station 24 includes connection terminal 90 that connects to hardwire connection 92 for transmitting signals to remote central station 12. In some embodiments, the emergency egress station includes wireless communication circuitry and an antenna in lieu of or in addition to a hardwire connection to provide wireless transmission of the signal to remote central station 12.

As in other emergency equipment stations described above, communications circuitry 52 is configured to continuously transmit a signal indicating ambient air temperature near the emergency egress station to the remote central station 12. In addition, communications circuitry 52 is configured to initiate a signal sent from emergency egress station 24 to remote central station 12 upon the detection of one or more of the predetermined external conditions associated with the station, such as an obstruction detected by the sonar module through apertures or windows 78. In other embodiments, the communications circuitry may be configured to initiate a signal to remote central station 12 upon detection of predetermined internal conditions associated with the station 24, such as a battery needing replacement or recharging, or a strobe light needing replacement. Additionally, emergency egress station 24 may include an audible signaling device (e.g., a speaker) for emitting an audible tone, signal, or message to alert facility personnel and/or the general public in the vicinity that the station is currently obstructed or that another predetermined internal or external condition has occurred. Also, emergency egress station 24 may include one or more additional strobes, or other similar lighting devices, for emitting a visual alert to indicate, e.g., that emergency egress station 24 is obstructed or in the event of an emergency, as communicated by a signal received via hardwire connection 92 or an antenna.

In this particular embodiment housing 108 includes terminal 112 that connecting wire 114 between housing 108 and strobe 110 so that the strobe is activated by a signal from the housing. Alternatively, an antenna (which may be either external to the housing or included within in the housing) can establish a wireless link between the housing and the strobe 110 such that a wireless signal transmitted from the housing activates the strobe. Also, in some embodiments, strobe 110 is activated by a signal initiated by another signal received by housing 108. For example, in some embodiments, housing 108 is in communication with emergency equipment such as a fire alarm pull station, defibrillator, smoke detector, or other emergency equipment providing a signal to activate strobe 110 in the event of an emergency.

Similar to docking station 76 (shown in FIG. 3), in some embodiments, housing 108 is fixedly mounted to the wall, W, with or without strobe 110, at a predetermined position spaced from a fire extinguisher, fire alarm pull station, defibrillator, or other piece of emergency equipment. So, for example, rather than incorporating the components of docking station (e.g., temperature sensor 42, sonic sensor 44, apertures 78, communications circuitry 52, etc.) into a housing positioned in close proximity to the emergency equipment, or incorporated into the emergency equipment, the components are incorporated into housing 108 that is positioned a distance away from the equipment and in communication with the emergency equipment via hardwire connection 92 or by wireless link established with an antenna. By communicating with the emergency equipment in the event of an emergency (e.g., a fire alarm pull station is pulled), a signal is sent from the emergency equipment to housing 108 to activate strobe 110 or, for example, in response to receiving the signal, the housing sends a signal over hardwire connection 92 to remote central station 12, or both.

Figure 11A:
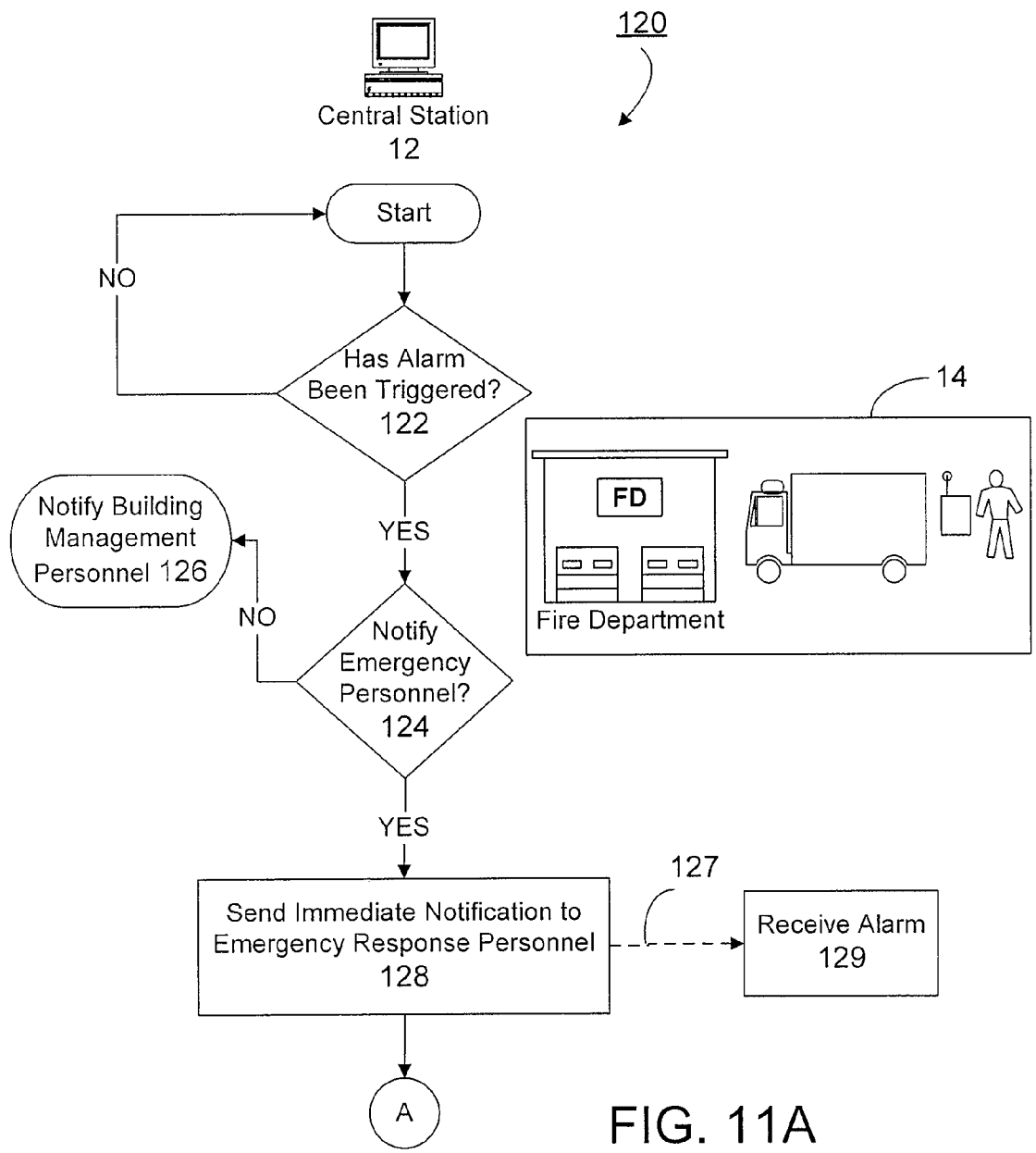
FIGS. 11A-11B is a flow chart showing a process for communicating sensory information to emergency response personnel.
Figure 11B:
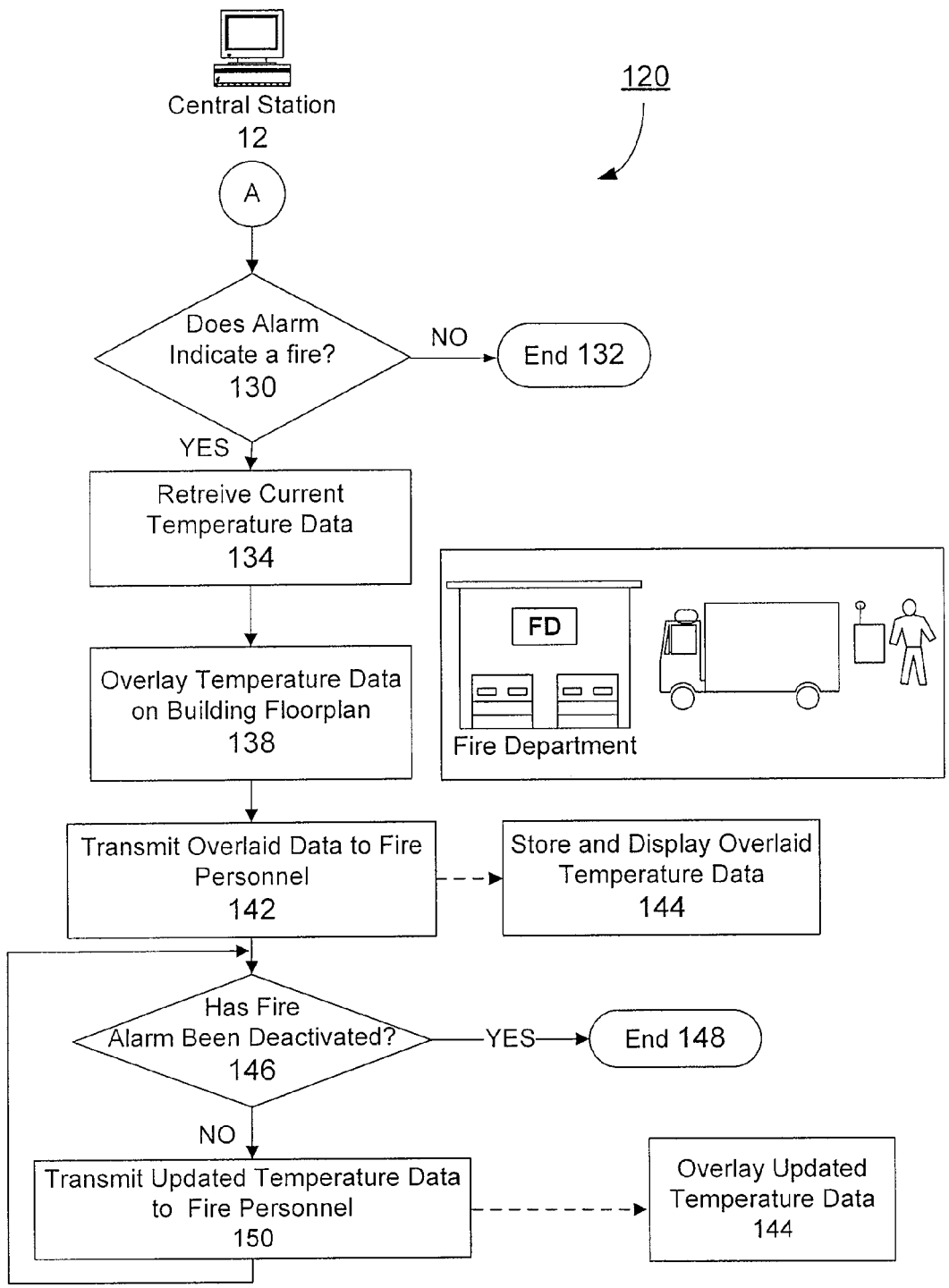

Referring to FIGS. 11A-11B, in a process (120) for communicating sensory data to emergency response personnel 14, remote central station 12 senses if an alarm has been triggered (122). In this implementation, an alarm is triggered when an emergency equipment station transmits a signal to the central station indicating the occurrence of certain internal or external conditions. For example, in fire extinguisher station 18 shown in FIGS. 2-3, an alarm is considered to be triggered when fire extinguisher station 18 transmits a signal indicating an out-of-range pressure condition, removal of the extinguisher from its installed position, or presence of an obstruction restricting access to station 18. In addition, remote central station 12 is also preferably in communication with the other emergency systems associated with building 14, such as a smoke alarm system, sprinkler system, and/or carbon monoxide alarm system, so that remote central station 12 receives an indication when an alarm is triggered by another emergency system.

If an alarm has been triggered, remote central station 12 determines (124) if emergency response personnel 14 should be notified of the alarm. In this embodiment, some alarms do not trigger immediate notification of emergency response personnel. For example, if an emergency equipment station transmits (i) a signal indicating a low battery condition or (ii) a signal indicating an out-of-range pressure condition in a fire extinguisher tank, a notification message is not sent to emergency response personnel, but rather is communicated (126) to building management personnel through, e.g., remote central station 12. However, remote central station 12 is configured to send immediate notification to emergency response personnel upon detection of other alarms. For example, if a signal is received at remote central station 12 indicating (i) a fire alarm pull station has been pulled, (ii) a fire extinguisher has been removed from its installed position, (iii) a defibrillator has been discharged, remote central station 12 will generate and transmit a notification message to emergency response personnel. Additionally, if remote central station 12 receives an indication that another emergency systems in building 14 (e.g., a smoke detection system, sprinkler system, carbon monoxide detection system, etc.) has been activated or (iv) a signal indicating the presence of an obstruction restricting access to the station, remote central station 12 will generate and send a notification message to emergency response personnel.

Upon determining that emergency response personnel are to be notified of an alarm, remote central station 12 generates and sends (128) an immediate message (127) to emergency response personnel 14 indicating an alarm has been activated. The message is received (129) by a communications device (e.g., dial-up modem, DSL modem, cable modem, network interface card, etc.) associated with emergency response personnel. A computer (e.g., a desktop computer located at the fire station, portable computer located in a fire truck, handheld computer carried with fire personnel, etc.) in communication with the communications device displays the message on a display screen (e.g., a monitor, LCD display, etc.). In other embodiments, the computer associated with emergency response personnel may trigger an audible alarm when an alarm message is received.

The message transmitted to emergency response personnel also preferably includes information about the source of the alarm (e.g., fire alarm triggered by smoke detector system, fire alarm triggered by removal of fire extinguisher, fire alarm triggered by fire alarm pull station, fire alarm triggered by carbon monoxide detector system, alarm triggered by discharge of defibrillator, etc.) as well as information about the location at which the alarm was triggered (e.g., a defibrillator station in room 206 on the second floor, a fire extinguisher station on the fourth floor, etc.). The source and location of the alarm may be quickly determined by remote central station 12 by matching identification information (e.g., a network address) included in the signal received from an emergency equipment station or other source with a corresponding identifier in the installed location database 56 (shown in FIG. 2). The message transmitted to emergency response personnel may include a graphical map (e.g., generated using an floor plan of the building) showing the location of the source of the alarm. In other implementations, the message transmitted to emergency response personnel may include a table or chart showing the location of the source of the alarm.

If the alarm sensed by remote central station 12 is one that indicates a fire condition (130) (e.g., an alarm signal indicating removal of a fire extinguisher from its installed position, alarm triggered by an activation of a fire alarm pull station, alarm from smoke detector or carbon monoxide detector systems indicating smoke or carbon monoxide, alarm from sprinkler system indicating activation of sprinklers), remote central station 12 retrieves (134) the latest temperature data received and stored from the network of emergency equipment stations. In this implementation, remote central station 12 also retrieves the floor plan of building 14 from data file 58 stored in storage device 55 (shown in FIG. 2). Remote central station 12 overlays (138) current temperature data on the building floor plan to generate a graphical temperature map of the building.

Remote central station 12 then transmits (142) a message including the graphical temperature map to a communications device associated with emergency response personnel. A computer in communication with the communications device displays the graphical temperature map on a display (e.g., a monitor, LCD display, etc.).

Remote central station 12 continuously or periodically (e.g., every 30 seconds) transmits updated temperature data (150) to a communication associated with the emergency response personnel where it is overlaid (144) on the graphical temperature map until (146) the alarm has been deactivated. It should be noted that temperature data includes not only actual temperature data received from the emergency equipment stations, but also data indicating that a emergency equipment station is no longer transmitting temperature data. Information that an emergency equipment station is no longer transmitting temperature data (or any data) provides an indication that the equipment station has been severely damages, e.g., by fire.

In another embodiment, the building floor plan is stored on a storage device (e.g., hard drive, CD-ROM, etc.) in communication with a computer associated with the emergency response personnel configured to receive the temperature data from the central station. In this embodiment, remote central station 12 transmits the current temperature information to a communication device associated with the emergency response personnel, where it is overlaid with the floor plan of the building to create a graphical temperature map of the building. Because a data file containing a building floor plan may be large, storing the building floor plan locally at a computer associated with emergency response personnel eliminates the necessity of transferring a large data file from remote central station 12 to emergency response personnel 14 during an emergency.

In another embodiment, remote central station 12 is configured to transmit a message containing a textual description (e.g., a table) of the current temperature indicated by each of the emergency equipment stations in the network of emergency equipment station, which is ultimately displayed by computer associated with emergency response personnel.

Remote central station 12 is also configured to receive communications from a communications device associated with emergency response personnel. In one implementation, remote central station 12 is configured to receive a signal from emergency response personnel to open a lock box 38 (shown in FIG. 1) to allow emergency response personnel to access the building. In another embodiment, the central station is configured to receive a request from emergency response personnel for a current temperature map of the building, floor and/or room.

A number of embodiments of the invention have been described. Nevertheless, it will be understood that various modifications may be made without departing from the spirit and scope of the invention. For example, wireless signaling technology may incorporate telecommunication schemes (e.g., Bluetooth or similar) to provide point-to-point or multipoint communication connections among, e.g., fire extinguisher stations and/or other emergency equipment stations (e.g., a defibrillator station) and/or the remote central station. These telecommunication schemes may be achieved, for example, with local wireless technology, cellular technology, and/or satellite technology. The wireless signaling technology may further incorporate spread spectrum techniques (e.g., frequency hopping) to allow the emergency equipment stations to communicate in areas containing electromagnetic interference. The wireless signaling may also incorporate identification encoding along with encryption/decryption techniques and verification techniques to provide secure data transfers among the devices.

In other embodiments, the emergency equipment stations (e.g., a defibrillator station) and/or remote central station may include or otherwise be associated with a Global Positioning System (GPS). GPS may be used to determine, for example, the geographic location of each emergency equipment station and provide location coordinates, via the wireless signaling technology, to the other emergency equipment stations (e.g., the defibrillator station) and/or the remote central station. Thus, the GPS system may provide the location of the fire alarm pull stations and allow, for example, tracking of the frequency that stations located in a particular region of a facility are obstructed.

Also, the signaling may use networking techniques to provide one-directional and/or multi-directional communications among the devices. In one example, signals from emergency equipment stations may be networked asynchronously, such as in an asynchronous transfer mode (ATM). The signals may also be networked synchronously, such as, for example, in a synchronous optical network (SONET). In still another example, the signals may be transmitted over a landline in an integrated services digital network (ISDN), as well as over other similar media, for example, in a broadband ISDN (BISDN).

A remote central station for transmitting sensory data to emergency response personnel may also be employed for remote inspection of multiple facilities, each including multiple or a system of emergency equipment stations. Communication between emergency equipment stations and a remote central station, including hard-wire and wireless communication, may be carried on directly, or indirectly, e.g. via relaying devices, including other emergency equipment stations.

Accordingly, other embodiments are within the scope of the following claims.

What is claimed is:

1. A system for communicating information to emergency response personnel comprising:
    a fire extinguisher station that includes a fire extinguisher, first sensor capable of detecting an out-of-range pressure condition for a tank of the fire extinguisher, a second sensor capable of detecting a removal of the fire extinguisher from an installed position, a third sensor capable of detecting an obstruction to access to the fire extinguisher, and communications circuitry:
    a central station located remotely from the fire extinguisher station and in communication with the communications circuitry of the fire extinguisher station equipment station, the central station configured to receive an alarm from the fire extinguisher station, and further configured to create a notification to at least one of the emergency response personnel and building management personnel according to a type of the alarm; and
    an emergency lighting station coupled in a communicating relationship with the central station and configured to generate the alarm to the central station under one or more predetermined conditions, wherein the one or more predetermined conditions includes an obstruction of illumination of an area intended to be illuminated by the emergency lighting station.

2. The system of claim 1 wherein the communications circuitry includes wireless communications circuitry.

3. The system of claim 1 wherein the communications circuitry includes wired communications circuitry.

4. The system of claim 1 further comprising a defibrillator coupled in a communication relationship with the central station and configured to generate the alarm to the central station under one or more predetermined conditions.

5. The system of claim 4 wherein the one or more predetermined conditions includes a removal of the defibrillator from a defibrillator installed position.

6. The system of claim 4 wherein the one or more predetermined conditions includes a low battery condition of the defibrillator.

7. The system of claim 4 wherein the one or more predetermined conditions includes an obstruction to access to the defibrillator.

8. The system of claim 1 further comprising a smoke detector coupled in a communicating relationship with the central station and configured to generate the alarm to the central station under one or more predetermined conditions.

9. The system of claim 8 wherein the one or more predetermined conditions includes a low battery condition of the smoke detector.

10. The system of claim 1 further comprising an emergency egress station that provides illumination in the event of an emergency, the emergency egress station coupled in a communicating relationship with the central station and configured to generate the alarm to the central station under one or more predetermined conditions.

11. The system of claim 10 wherein the one or more predetermined conditions includes an obstruction of an emergency exit way identified by the emergency egress station.

12. The system of claim 10 wherein the emergency egress station is configured to receive a remote activation signal from the central station.

13. The system of claim 1 further comprising a fire alarm pull station coupled in a communicating relationship with the central station.

14. The system of claim 1 wherein the alarm includes data correlated to a location of the fire extinguisher.

15. The system of claim 14 wherein the fire extinguisher includes a Global Positioning System.

16. The system of claim 15 wherein the Global Positioning System determines a geographic location of the fire extinguisher.

17. The system of claim 16 wherein the fire extinguisher communicates the geographic location to the fire extinguisher station, and wherein the fire extinguisher station transmits the geographic location to the central station.

18. A system for communicating information to emergency response personnel comprising:
    a fire extinguisher station that includes a fire extinguisher, first sensor capable of detecting an out-of-range pressure condition for a tank of the fire extinguisher, a second sensor capable of detecting a removal of the fire extinguisher from an installed position, a third sensor capable of detecting an obstruction to access to the fire extinguisher, and communications circuitry: and
    a central station located remotely from the fire extinguisher station and in communication with the communications circuitry of the fire extinguisher station equipment station, the central station configured to receive an alarm from the fire extinguisher station, and further configured to create a notification to at least one of the emergency response personnel and building management personnel according to a type of the alarm, wherein the central station is configured to receive communications from a communications device associated with the emergency response personnel to open a lock box, thereby allowing access to a building that contains the fire extinguisher station.

19. The system of claim 18 wherein the notification includes a notification to the emergency response personnel that an emergency system has been activated.

20. A system for communicating information to emergency response personnel comprising:
    a fire extinguisher station that includes a fire extinguisher, first sensor capable of detecting an out-of-range pressure condition for a tank of the fire extinguisher, a second sensor capable of detecting a removal of the fire extinguisher from an installed position, a third sensor capable of detecting an obstruction to access to the fire extinguisher, and communications circuitry:
    a central station located remotely from the fire extinguisher station and in communication with the communications circuitry of the fire extinguisher station equipment station, the central station configured to receive an alarm from the fire extinguisher station, and further configured to create a notification to at least one of the emergency response personnel and building management personnel according to a type of the alarm; and an emergency egress station that provides illumination in the event of an emergency, the emergency egress station coupled in a communicating relationship with the central station and configured to generate the alarm to the central station under one or more predetermined conditions, wherein the emergency egress station is configured to receive a remote activation signal from the central station.

* * * * *